(12) United States Patent
Chen et al.

(10) Patent No.: US 8,673,640 B2
(45) Date of Patent: Mar. 18, 2014

(54) POROUS SCAFFOLD, METHOD OF PRODUCING THE SAME AND METHOD OF USING THE POROUS SCAFFOLD

(75) Inventors: Guoping Chen, Ibaraki (JP); Tetsuya Tateishi, Ibaraki (JP); Junzo Tanaka, Ibaraki (JP)

(73) Assignee: National Institute for Materials Science, Ibaraki (JP)

( * ) Notice: Subject to any disclaimer, the term of this patent is extended or adjusted under 35 U.S.C. 154(b) by 1018 days.

(21) Appl. No.: 11/992,216

(22) PCT Filed: Sep. 20, 2006

(86) PCT No.: PCT/JP2006/318651
§ 371 (c)(1),
(2), (4) Date: Jun. 27, 2008

(87) PCT Pub. No.: WO2007/034843
PCT Pub. Date: Mar. 29, 2007

(65) Prior Publication Data
US 2009/0233362 A1    Sep. 17, 2009

(30) Foreign Application Priority Data

Sep. 20, 2005 (JP) .................................. 2005-272429
Nov. 10, 2005 (JP) .................................. 2005-326719
Nov. 10, 2005 (JP) .................................. 2005-326720

(51) Int. Cl.
*C12N 5/00* (2006.01)
*C12N 5/02* (2006.01)
*A01N 1/00* (2006.01)
*A01N 1/02* (2006.01)

(52) U.S. Cl.
USPC ...... 435/395; 435/401; 435/283.1; 435/284.1

(58) Field of Classification Search
USPC .................................................. 435/174–180
See application file for complete search history.

(56) References Cited

U.S. PATENT DOCUMENTS 4,803,168 A * 2/1989 Jarvis, Jr. ..................... 435/357
5,893,888 A * 4/1999 Bell ............................... 424/423
5,916,585 A    6/1999 Cook et al.

(Continued)

FOREIGN PATENT DOCUMENTS

| EP | 1 273 312 | 1/2003 |
| JP | 2002-143290 | 5/2002 |
| JP | 2003-010309 | 1/2003 |
| WO | 97/46267 | 12/1997 |

OTHER PUBLICATIONS

International Search Report mailed Oct. 17, 2006 for International Application PCT/JP2006/318651.

(Continued)

*Primary Examiner* — Chris R Tate
*Assistant Examiner* — Douglas F White
(74) *Attorney, Agent, or Firm* — Wenderoth, Lind & Ponack, L.L.P.

(57) ABSTRACT

A porous scaffold having pores for seeding cells characterized in that, in the outer peripheral face of the porous main body having the pores for seeding cells, a porous membrane having pores smaller than the cells is located. Thus, it is possible to provide a porous scaffold whereby the cells can be seeded at a high efficiency while preventing cell leakage and, moreover, even cells having little adhesiveness can be adhered.

3 Claims, 8 Drawing Sheets

(56) References Cited

U.S. PATENT DOCUMENTS

| | | | |
|---|---|---|---|
| 5,972,332 A * | 10/1999 | Rees et al. | 424/93.7 |
| 6,143,293 A * | 11/2000 | Weiss et al. | 424/423 |
| 6,328,765 B1 * | 12/2001 | Hardwick et al. | 623/23.72 |
| 6,461,385 B1 * | 10/2002 | Gayer et al. | 623/23.51 |
| 6,689,608 B1 * | 2/2004 | Mikos et al. | 435/395 |
| 6,790,455 B2 * | 9/2004 | Chu et al. | 424/423 |
| 2003/0012805 A1 * | 1/2003 | Chen et al. | 424/423 |
| 2004/0241145 A1 * | 12/2004 | Hata et al. | 424/93.7 |
| 2005/0004242 A1 * | 1/2005 | Sotome et al. | 521/61 |
| 2005/0107286 A1 * | 5/2005 | Uemura et al. | 514/7 |

OTHER PUBLICATIONS

The 9th Annual Meeting of the Japanese Society for Tissue Engineering, p. 2-14, Kyoto, Japan, (Sep. 7, 2006), w/ English Translation.

Kawazoe, et al., "Culture of Mesenchymal Stem Cells in a Collagen Sponge to Reduce the Cell Leak," Polymer Preprints, Japan, vol. 55, No. 2, (2006) w/ English Translation.

Akahane, "Chondrogenic Differentiation of Mesenchymal Stem Cells Cultured in a Collagen Sponge," Biomaterials Center, National Institute for Materials Science, Dai 32 Kai Japanese Society for Clinical Biomechanics Program-Shorokushu, 2005 Nen 10 Gatsu 3 Nichi, p. 218 w/ English Translation.

Chen, et al., "A Hybrid Network of Synthetic Polymer Mesh and Collagen Sponge," The Royal Society of Chemistry, 2000, Chem. Commun., 2000, 1505-1506.

Chen, et al., "Redifferentiation of Dedifferentiated Bovine Chondrocytes when Cultured in Vitro in a PLGA-Collagen Hybrid Mesh," FEBS Letters 542 (2003) 95-99, Elsevier Science B.V. on behalf of the Federation of European Biochemical Societies.

* cited by examiner (A) FIRST POROUS BODY
(B) SECOND POROUS BODY
(C) THIRD POROUS BODY
(D) FOURTH POROUS BODY FORMED IN PORES OF PRIMARY STRUCTURAL BODY OF FIRST POROUS BODY
(E) FIFTH POROUS BODY FORMED IN PORES OF PRIMARY STRUCTURAL BODY OF SECOND POROUS BODY
(F) SIXTH POROUS BODY FORMED IN PORES OF PRIMARY STRUCTURAL BODY OF THIRD POROUS BODY (A) FIRST POROUS BODY
(B) SECOND POROUS BODY
(C) THIRD POROUS BODY
(D) FOURTH POROUS BODY FORMED IN PORES OF PRIMARY STRUCTURAL BODY
OF FIRST POROUS BODY

PERIPHERAL PART

CENTRAL PART

POROUS SCAFFOLD, METHOD OF PRODUCING THE SAME AND METHOD OF USING THE POROUS SCAFFOLD

BACKGROUND OF THE INVENTION (1) Field of the Invention

This invention relates to a porous scaffold having pores for seeding cells, a method of producing the same, and a method of using the porous scaffold. More specifically, this invention relates to a porous scaffold usable for seeding cells capable of differentiation and organization to form living tissues and organs such as bone, cartilage, ligament, skin, blood vessel, pancreas, and liver that are injured or lost due to disease, accident, and the like for the purpose of repairing the injured or lost tissues and organs, a method of producing the same, and a method of using the porous scaffold.

(2) Description of Related Art

As conventional methods for repairing and treating living tissues and organs such as cartilage, skin, bone, ligament, skin, blood vessel, pancreas, and liver that are injured or lost due to disease, accident, and the like, treatment methods by an artificial organ, organ transplantation, and the like have been known. However, in the case of the artificial organ, there are problems such as insufficient function, wearing, loosening, and breakage due to artificial member, and the like. Also, in the case of the organ transplantation, there is the problem of donor shortage, and, in the case where the donor is an unrelated person, rejection response clue to immunologic response is in question.

Due to the various problems, a treatment method by tissue engineering is considered to be ideal, and studies for regenerating a tissue to be transplanted by culturing cells of a patient in a porous scaffold are being actively conducted. As specific examples, firstly, a method wherein living cells are proliferated ex vivo and seeded in a porous scaffold that is used as a scaffold for the living cells or tissue for ex vivo culture, and the thus-formed living tissue is transplanted to the living body is known. Secondly, a method wherein living cells are seeded in a porous scaffold to be implanted into a living body for inducing regeneration of a living tissue in vivo is known. Thirdly, a method wherein a porous scaffold is directly implanted into an injured site to induce neighboring cells to enter the porous scaffold for inducing formation of a new tissue is known. Thus, the porous scaffold for inducing and promoting formation of living tissue and maintaining the shape of the living tissue has the remarkably important role. The porous scaffold is required to have biocompatibility as a property of not influencing on living bodies, bioabsorbability for allowing formation of new living tissue and capable of degradation and absorption, an appropriate mechanical strength, and the like.

As such scaffolds, porous materials of bioabsorbable polymers such as polylactic acid (PLA), polyglycolic acid (PGA), a copolymer of lactic acid and glycolic acid (PLGA), collagen, and the like have commonly been used in the art (see JP-A-2003-10309).

In the case of culturing cells by using the porous scafold of bioabsorbable polymer, the cells are seeded and adhered to the material. However, the number of cells to be collected from a patient is limited, and, in view of the fact that it is most desirable to seed and adhere all of the obtained valuable cells to the porous scaffold, it is remarkably important to seed and adhere any type of cells to the porous scaffold irrespective of easily-adherable cells and hardly-adherable cells.

However, in the case of seeding cells in the porous material of bioabsorbable polymer, cell leakage from a periphery of the porous material is violent, and it is difficult to seed cells at a high efficiency to porous scaffold having a low porosity. Further, in the case of hardly-adherable cells, almost all of the cells cannot adhere to the material to adversely affect on the regeneration of tissue and organ.

Osteoarthritis deformans is a disease frequently seen in the field of orthopedics and often involves severe dysfunction. Though prosthetic joint surgery is the mainstream of surgical treatment, currently available prosthetic joint parts made from metals and high molecular polymers have the above-described problems of infection, wearing, loosening, and breakage. In the case of tissue transplantation, there are problems of donor shortage and rejection reaction based on immunological response, too. Due to existence of the various problems, the treatment methods by the approach of tissue engineering is now considered to be ideal, and studies on regeneration of cartilage tissue are being actively conducted.

In order to regenerate a cartilage tissue by the approach of tissue engineering, a three-dimensional porous scaffold is required as a scaffold for chondrocytes or stem cells differentiatable into chondrocytes to proliferate and a support for a living tissue being formed.

However, since a central part and a surface layer of a conventional porous scaffold have almost identical porous structures, seeded cells do not stay in the porous scaffold, and a large part of the cells passes through openings and slits that are larger than the size of the cell to leak from a periphery of the porous scaffold. Accordingly, it is remarkably difficult to efficiently seed the chondrocytes or the stem cells differentiatable into chondrocytes in the culturing porous scaffold, and, therefore, it is impossible to obtain an effective cell seeding efficiency and to accumulate the cells in the culturing porous scaffold by a large scale, thereby adversely affecting on the cartilage tissue regeneration.

Also, since neighboring different tissues have been regenerated in identical porous scaffold, such environment is different from the neighboring structure in a living tissue or organ where different tissues are combined and multilayered. Also, in order to simultaneously regenerate neighboring tissues, it is desirable to use a porous scaffold having materials and structures suitable for regenerating both of the tissues.

DISCLOSURE OF INVENTION

Problems to be Solved by the Invention

Therefore, in order to solve the conventional problems, an object of this invention is to provide a porous scaffold capable of suppressing leakage of cells, seeding the cells highly efficiently, and adhering hardly-adherable cells, a method of producing the same, and a method of using the porous scaffold.

Another object of this invention is to provide a porous scaffold having a good biocompatibility and suitably used for regeneration of each of neighboring tissues, a method of producing the same, and a method of using the porous scaffold.

Means for Solving the Problems

According to this invention, the following technological means will be provided for the purpose of solving the above-described problems.

(1) A porous scaffold having pores for seeding cells characterized in that, in an outer peripheral face of a porous main body having the pores for seeding cells, a porous membrane having pores smaller than the cells is located.

(2) The porous scaffold according to item (1), characterized in that the main body has a frame-like framework.

(3) The porous scaffold according to item (1), characterized in that the main body has a cage-like framework.

(4) The porous scaffold according to any one of items (1) to (3), characterized in that the porous membrane is a bioabsorbable substance or a non-bioabsorbable substance.

(5) The porous scaffold according to any one of items (1) to (4), characterized in that a membrane-like porous body is laminated on the porous membrane.

(6) The porous scaffold according to item (5), characterized in that a plurality of layers of the membrane-like porous body are located to be multilayered.

(7) The porous scaffold according to item (3), characterized in that the cage-like main body is further filled with a porous substance.

(8) The porous scaffold according to item (7), characterized in that the porous substance is a bioabsorbable substance.

(9) The porous scaffold according to item (4) or (8), characterized in that the bioabsorbable substance is at least one selected from the group consisting of a bioabsorbable synthetic polymer, a bioabsorbable natural polymer, a cell growth factor, a cell differentiation control factor, and derivatives thereof.

(10) The porous scaffold according to any one of items (1) to (8), characterized by having a multilayer structure comprising layers having different characteristics.

(11) The porous scaffold according to item (10), characterized in that the multilayer structure is obtainable by lamination, inclusion, coating, contact of particles or lumps, three-dimensional or two-dimensional pattern contact, or combination of two or more thereof.

(12) The porous scaffold according to item (10) or (11), characterized in that the layers forming the multilayer structure are different in at least one of composition, porous structure including porosity, size of pores, continuity of pores, and mechanical property.

(13) The porous scaffold according to any one of items (1) to (12), characterized in that the main body is at least one selected from the group consisting of a bioabsorbable synthetic polymer, a bioabsorbable natural polymer, a cell growth factor, a cell differentiation control factor, and derivatives thereof.

(14) The porous scaffold according to any one of items (10) to (12), characterized in that at least one of the layers of the multilayer structure comprises at least one selected from the group consisting of a bioabsorbable synthetic polymer, a bioabsorbable natural polymer, a cell growth factor, a cell differentiation control factor, and derivatives thereof.

(15) A production method of the porous scaffold defined in any one of items (1) to (14), characterized by using a main body having a framework structure and by laminating a porous membrane on a surface of the framework structure.

(16) A method of using the porous scaffold defined in any one of items (1) to (14), characterized by causing the main body to carry chondrocytes or stem cells differentiating into chondrocytes.

Effect of the Invention

According to this invention, since a structure wherein a main body is covered with a porous membrane having pores smaller than the size of cells is used, a fear for leakage of cells seeded in the main body to the outside is eliminated, and it is possible to accelerate regeneration of a tissue, thereby making it possible to remarkably efficiently seed the cells to be regenerated.

Also, according to this invention, by achieving the multilayer structure, it is possible to regenerate a multilayered living tissue and organ such as bone, cartilage, ligament, skin, blood vessel, pancreas, and liver, and application to treatments of diseases of cartilage, ligament, blood vessel, pancreas, liver, and the like is greatly expected.

DETAILED DESCRIPTION OF THE INVENTION

Figure 1:
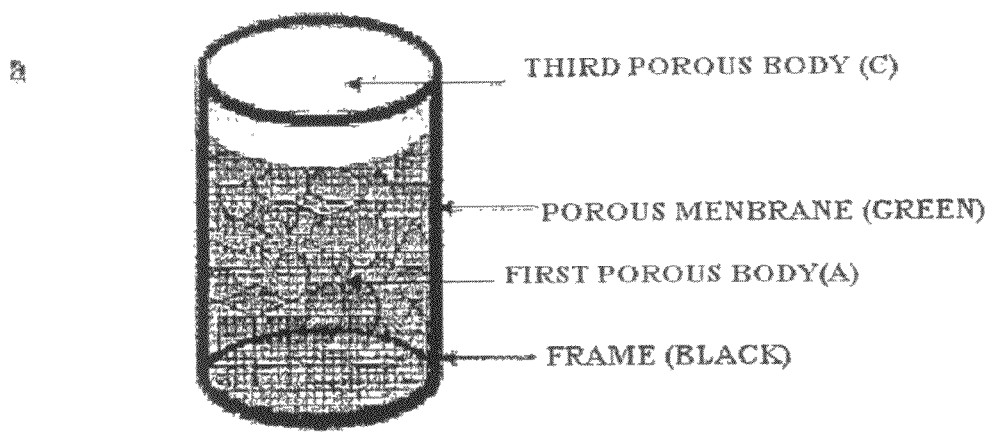
FIG. 1 is a diagram showing Representative Example 1 of a columnar porous scaffold covered with a porous membrane and having a multilayer structure.
Figure 1:
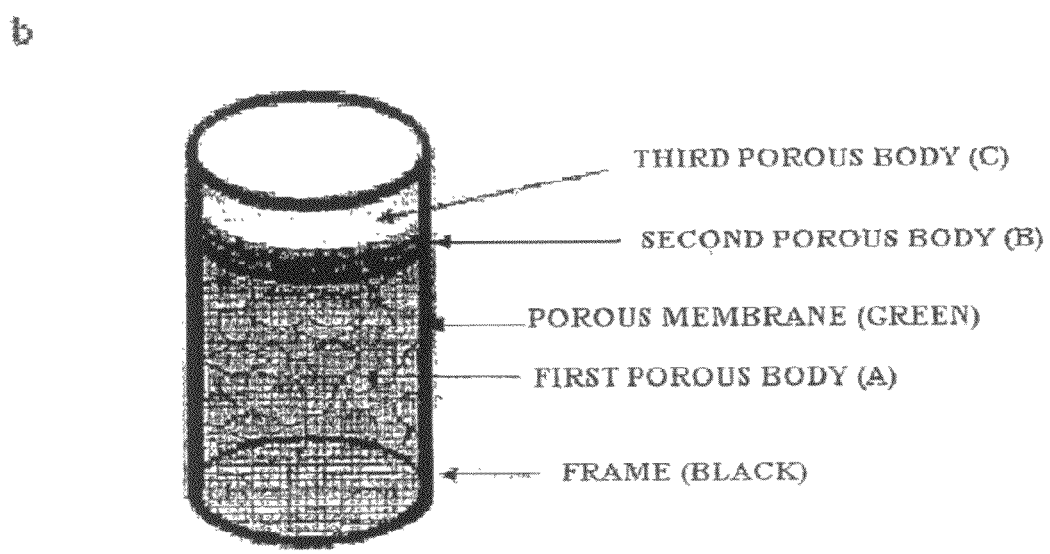

Hereinafter, embodiments of this invention will be described in detail.

A porous scaffold capable of carrying and culturing cells is formed of a main body and a porous membrane.

The porous membrane has dense pores having a pore size that is smaller than the size of the cells. A porosity of the porous membrane may preferably be 10% to 99%, and a most desirable porosity is 30% to 99%. The pore size of the porous membrane may preferably be from 0.1 to 30 µm that is smaller than the cells, and a most desirable pore size is from 0.45 to 10 µm. The pores having such size make it possible to allow a cell suspension to reach cells to enter the inner part of the porous scaffold when the cell suspension is delivered into the porous scaffold by drops. Such porous membrane also makes it possible to maintain the shape of a regenerated tissue.

A material for the porous membrane may be a bioabsorbable polymer or a non-bioabsorbable polymer such as a nylon mesh and a sponge.

Examples of the bioabsorbable polymer include polylactic acid, polyglycolic acid, a copolymer of lactic acid and glycolic acid, poly-ε-caprolactone, polyester or cellulose such as copolymers of the above bioabsorbable polymers, polysaccharide such as polyalginic acid, and the like. Examples of the non-bioabsorbable polymer include nylon, polyethylene, polypropylene, polystyrene, and the like. Preferred among the above-described bioabsorbable polymers in this invention are the polylactic acid, the copolymer of lactic acid and glycolic acid, the poly-ε-caprolactone, and the copolymers thereof, and preferred among the above-described non-bioabsorbable polymer is the nylon.

In this invention, the main body is covered with the porous membrane, but an entrance for seeding cells is not covered with the porous membrane. The porous membrane may be a single layer or may have a multilayer structure having two or more layers. In the case of the two or more layers, it is sufficient when the innermost layer has the porous structure, and a structure wherein all of the layers have the porous structure may also be used. The innermost membrane functions to prevent the cells from leaking by being in close contact with the main body formed at a central part.

In the porous scaffold of this invention, the main body may preferably have a frame-like or cage-like framework. The porous scaffold of this invention is formed by locating the porous membrane on an outer peripheral face of the porous scaffold along the shape of the frame-like or cage-like framework. The size and the shape of the framework are molded in such a manner as to match the size and the shape of a tissue such as a cartilage tissue to be regenerated. For example, the size and the shape of the framework are decided in view of a thickness, a curvature, and the like of the cartilage tissue to be regenerated.

In the case of preparing the framework from the bioabsorbable material, the outer size and the outer shape of the framework should be the same as the thickness and the curvature of the cartilage tissue to be regenerated. In the case of preparing the framework from the non-bioabsorbable material, the inner size and the inner shape of the framework should be the same as the thickness and the curvature of the cartilage tissue to be regenerated. With such constitution, shape abnormality due to regeneration hardly or never occurs, and it is possible to regenerate a shape similar to that of defected or lost tissue.

Also, an inner part of the framework is filled with a porous body having pores of the size enabling cell seeding. As the porous body, at least one selected from the group consisting of a bioabsorbable synthetic polymer, a bioabsorbable natural polymer, a cell growth factor, a cell differentiation control factor, and derivatives thereof may be used.

The porous body has a function of supporting adhesion of cells and promoting proliferation, differentiation, extracellular matrix secretion, and tissue regeneration as a scaffold to which the cells adhere. The porous body is closely linked with the frame-like or cage-like framework on which the membrane having the porous structure is located, so that the porous body and the framework do not separated from each other during the course of cell seeding and cell culture.

Examples of the bioabsorbable synthetic polymer for forming the porous body include polylactic acid, polyglycolic acid, a copolymer of lactic acid and glycolic acid, poly-ε-caprolactone, polyester or cellulose such as copolymers of the above bioabsorbable polymers, polysaccharide such as polyalginic acid, and the like. Preferred among the above-described bioabsorbable synthetic polymers in this invention are the polylactic acid, the polyglycolic acid, the copolymer of lactic acid and glycolic acid, the poly-ε-caprolactone, and the copolymers thereof.

Any of bioabsorbable natural polymers existing naturally or derived from a living body and having biocompatibility may be used as the bioabsorbable natural polymer for forming the porous body, and at least one selected from the group consisting of collagen, hyaluronic acid, proteoglycan, aggrecan, chondroitin sulfate, gelatin, fibronectin, laminin, and the like, particularly collagen, may preferably be used. Collagen includes type I, II, III, IV, V, VI, VIII, IX, and X collagens and the like. In this invention, any of these collagens may be used, and derivatives of the collagens may also be used.

In general, the bioabsorbable natural polymers are high in porosity and cell seeding efficiency as compared to the bioabsorbable synthetic polymers and excellent from this point of view. In turn, the bioabsorbable synthetic polymers are high in mechanical strength as compared to the bioabsorbable natural polymers. Therefore, the porous scaffold of this invention will have appropriate porosity, cell seeding efficiency, and mechanical strength through combination of the bioabsorbable natural polymer and the bioabsorbable synthetic polymer as required. For example, a structure wherein the innermost layer is formed from the bioabsorbable synthetic polymer and the bioabsorbable natural polymer is laminated on the innermost layer may be used.

As the cell growth factor and the cell differentiation control factor for forming the porous body, any of those capable of controlling growth and differentiation of cells may be used, and at least one selected from the group consisting of an epidermal cell growth factor (EGF), insulin, a platelet-derived growth factor (PDGF), a fibroblast growth factor (FGF), a hepatocyte growth factor (HGF), a vascular endothelial growth factor (VEGF), a β-transforming growth factor (TGF-β), a bone morphogenetic factor (BMP), dexamethasone, and the like or derivatives thereof may be used.

Pores of the porous body are used as the scaffold for adhesion, proliferation, and tissue regeneration of seeded cells and may preferably be continuous. The size of each of the pores may be about 1 to 1,000 μm, preferably about 20 to 400 μm.

Also, a thickness of the porous body in this invention may appropriately be decided depending on a usage mode of the biocomplex material and may ordinarily be 0.1 to 10 mm, preferably 0.1 to 50 mm. A diameter, a width, or a depth may ordinarily be 0.1 to 100 mm, preferably 0.1 to 50 mm. A porosity thereof may ordinarily be 50% to 99.9%, preferably 90% to 99.9%.

Figure 4:
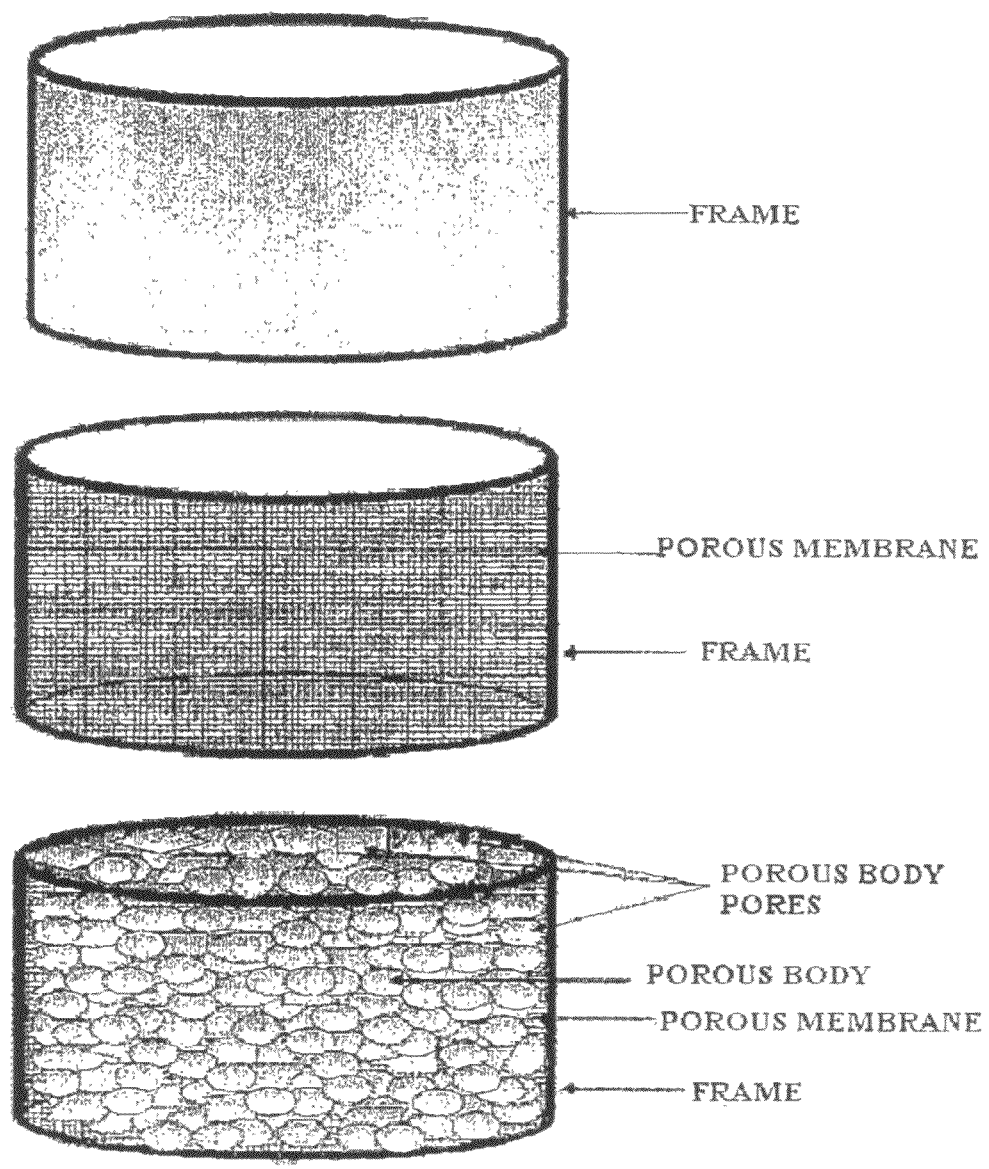
FIG. 4 is a diagram showing a columnar porous scaffold covered with a porous membrane and having a single porous structure.
Figure 5:
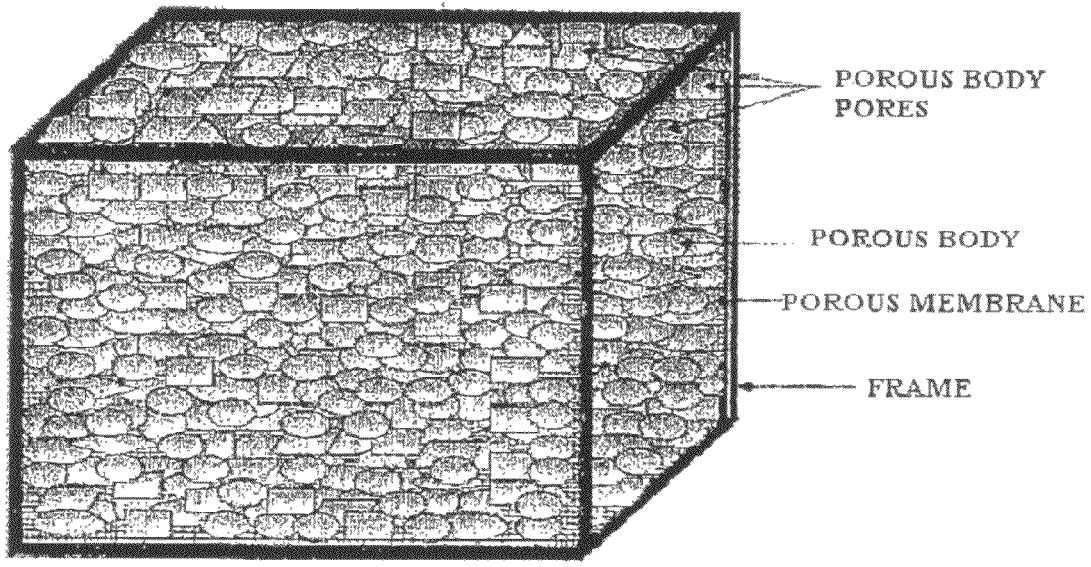
FIG. 5 is a diagram showing a cubic porous scaffold covered with a porous membrane and having a single porous structure.

A method for producing the porous scaffold having the multilayer structure of this invention may be such that (1) after forming a porous body (mesh, sponge, or the like), a porous columnar body (see FIG. 4), or a porous rectangular parallelepiped or cubic body of the bioabsorbable polymer or the non-bioabsorbable polymer, (2) a membrane having a dense porous structure of the bioabsorbable polymer or the non-bioabsorbable polymer is attached to an inner side and a bottom face of the columnar, rectangular parallelepiped, or cubic body with heat, a glue, or an organic solvent, (3) and a solution of at least one selected from the group consisting of the bioabsorbable natural polymer, the cell growth factor, the cell differentiation control factor, the derivatives thereof and the like is placed, (4) followed by freeze-drying and, preferably, crosslinking through a treatment using a gaseous or liquid crosslinking agent and heat.

Though various methods may be employed for the treatment method (3) of using the aqueous solution of the bioabsorbable natural polymer, the cell growth factor, the cell differentiation control factor, or the derivatives thereof, impregnation may preferably be used.

The impregnation is effective in the case where a concentration or a viscosity of the aqueous solution of the bioabsorbable natural polymer, the cell growth factor, the cell differentiation control factor, or the derivatives thereof is low, and, more specifically, the impregnation may be performed by impregnating the porous body (mesh, sponge, or the like), the porous columnar body, or the porous rectangular parallelepiped or cubic body of the bioabsorbable polymer or the non-bioabsorbable polymer with a low concentration aqueous solution of the bioabsorbable natural polymer, the cell growth factor, the cell differentiation control factor, or the derivatives thereof. By performing degassing under reduced pressure, the porous body (mesh, sponge, or the like), the porous columnar body, or the porous rectangular parallelepiped or cubic body of the bioabsorbable polymer or the non-bioabsorbable polymer is filled with the low concentration aqueous solution of the bioabsorbable natural polymer, the cell growth factor, the cell differentiation control factor, or the derivatives thereof.

As the crosslinking agent to be used in this invention, any of conventional crosslinking agents may be used. Preferred crosslinking agent may be aldehydes such as glutaraldehyde, formaldehyde, and paraformaldehyde, and a particularly preferred crosslinking agent is glutaraldehyde.

The crosslinking agent may preferably be used in the form of a gas for crosslinking in this invention. Specifically, when crosslinking the porous body formed of the bioabsorbable natural polymer, the crosslinking is performed under an atmosphere of the crosslinking agent having a constant concentration at a constant temperature or under an atmosphere of a crosslinking agent vapor saturated with an aqueous solution of the crosslinking agent.

The crosslinking temperature should be selected within the range in which the porous body formed of the bioabsorbable polymer is not melted and the crosslinking agent vapor is formed and is ordinarily set to 20° C. to 50° C.

A crosslinking time may be varied depending on the type of the crosslinking agent and the crosslinking temperature, and it is desirable to set the crosslinking temperature within the range in which compatibility and bioabsorbability of the natural polymer porous body are not inhibited and crosslinking and fixing that does not cause the natural polymer porous body to melt during living donor transplantation is performed.

When the crosslinking time is short, the crosslinking becomes insufficient to raise a risk of melting of the porous body formed of the bioabsorbable natural polymer in the living body in a short time after the transplantation. Though the crosslinking is promoted along with an increase in crosslinking time, a too long crosslinking time is undesirable since the too long crosslinking time causes problems such as deterioration of compatibility, reduction in seeding density of osteogenic cells and chondrogenic cells in the scaffold material, inefficient cell proliferation and tissue regeneration, and reduction in bioabsorbability. A preferred crosslinking time is about 10 minutes to 12 hours.

The porous scaffold of this invention may be used as a cell scaffold material, i.e. as a culture carrier, when various cells or a cell solution to be seeded containing cells are seeded in the porous scaffold. Also, by using the porous scaffold for carrying and culturing the cells, it is possible to organize the cells and to use the organized cells as a regenerated graft to be utilized in medical practice by directly transplanting the organized cells to a living body.

The cells usable as the culture object in this invention are not particularly limited. For example, animal-derived cells, plant-derived cells, and microorganism-derived cells may be cultured. Among others, the animal-derived cells are preferred, and mammal-derived cells are particularly preferred. Examples of the mammal include human, cow, monkey, dog, sheep, goat, rat, mouse, rabbit, and the like.

Of course, cells of any origin may be used as the cells in this invention without limitation to the cells having the above-described origins. For example, fusion cells of cells of different origins or of cells and a non-cellular material such as a collagen gel membrane, a cocoon filament, and a nylon mesh may be used. Tissues and organs such as liver, heart, kidney, skin, bone, cartilage, bone marrow, and blood vessel of animals and cells derived from tissues such as a tissue derived from any of the above-listed tissues may be used. Further, primary cells and a cell strain may be used. Examples of the primary cells in the animal cells include chick embryo-derived cells (PSG), rat primary cardiomyocytes, rat primary hepatocytes, mouse primary myeloid cells, pig primary hepatocytes, cow vascular endothelial cells, human primary cord blood cells, human primary myelopoietic cells, and human primary nerve cells such as dorsal root ganglion cells (DRG), and the like.

Examples of the cell strain include CHO cells derived from Chinese hamster ovary cells, HeLa cells derived from human uterus cancer, Huh7 cells and HepG2 cells derived from human liver cancer, and the like. Other examples include embryo-stem cells (ES cells) and tissue stem cells obtained from mouse, chicken, pig, human, and the like and cells differentiated from the ES cells and the tissue stem cells. Also, it is possible to culture cells obtained by gene engineering such as plasmid introduction and virus infection of these cells in the porous scaffold of this invention.

As a specific example of preparation of the cell solution to be seeded in the case of chondrocytes, a living cartilage tissue is subjected to extracellular matrix decomposition through an enzyme treatment using collagenase, trypsin, lipase, proteinase, or the like, followed by adding a serum medium, and the chondrocytes are isolated by centrifugation. The isolated chondrocytes are seeded in a culture flask to be cultured in a DMEM medium (DMEM serum medium) containing a 10%-fetal bovine serum, 4,500 mg/L of glucose, 584 mg/L of glutamine, 0.4 mM of proline, and 50 mg/L of ascorbic acid. A passage culture is performed for a few times until the sufficient number of cells is obtained, and the cells obtained by the passage cultures are collected by a trypsin treatment to be used for the cell solution to be seeded and cultured.

It is possible to prepare the chondrocytes and the stem cells differentiating into chondrocytes to be used in this invention from a living tissue by an ordinary method.

The stem cells differentiating into chondrocytes are isolated by centrifuging a bone marrow extract liquid by density gradient centrifugation using a density gradient medium formed from a percoll or by ordinary centrifugation. These cells are seeded in a culture flask, and a passage culture is performed for a few times in a DMEM serum medium until the sufficient number of cells is obtained. The cells obtained by the passage cultures are collected by a trypsin treatment to be used for a cell solution to be seeded.

Further, the regenerated graft of cartilage tissue of this invention is characterized in that the chondrocytes or the stem cells differentiating into chondrocytes are carried by the porous scaffold for cells having the porous property as described above. Since such regenerated graft has a cartilage tissue similar to the three-dimensional structure originally possessed by living bodies, it is possible to use the regenerated graft for repairing cartilage defect due to a disease such as osteoarthritis or an accident.

A method for producing the regenerated graft is such that, for the purpose of seeding the chondrocytes or the stem cells differentiating into chondrocytes in the porous scaffold having the porous property for cells as described above, the cell solution to be seeded is added by dropping to a cell seeding face (on which the membrane having the dense porous structure with small pores is not attached) of the porous scaffold that has been wetted with a culture medium.

A cell concentration of the cell suspension solution to be seeded may ordinarily be $1 \times 10^3$ to $5 \times 10^8$ cells/mL, preferably $1\times10^4$ to $5\times10^7$ cells/mL, and it is desirable that a volume of the cell suspension solution to be seeded is equal to or more than a volume of the porous scaffold.

In the case of using the chondrocytes, the graft for regenerating cartilage tissue of this invention is obtainable by adding the cell suspension solution to be seeded by dropping to the three-dimensional porous substance, followed by further adding a culture medium, and culturing and proliferating the chondrocytes in the three-dimensional porous substance in a DMEM serum medium in an incubator at 37° C. and under a 5%-$CO_2$ atmosphere.

In the case of using the stem cells, a process for differentiation into chondrocytes is required, and the graft is obtainable by adding a cell suspension solution for seeding the stem cells differentiating into the chondrocytes by dropping to the three-dimensional porous substance, and culturing and proliferating the cells in a DMEM serum medium for 1 to 2 weeks, followed by differentiation by culturing in a DMEM medium (differentiation medium) containing 4,500 mg/L of glucose, 584 mg/L of glutamine, 0.4 mM of proline, 50 mg/L of ascorbic acid, and a transforming growth factor-β3 (TGF-β3) for 1 to 2 weeks.

The thus-obtained regenerated graft of cartilage tissue is transplanted into a living body as it is. In this case, it is more preferable that a frame part serving as a framework of the carrier, i.e. the frame-like part or the cage-lie part, is formed from the bioabsorbable substance like the porous substance or formed from a material having high compatibility with the living body.

As a procedure before implantation, a cartilage tissue regenerated in the carrier may be collected from the carrier to be implanted. As a method for collection, collection by breaking a frame part which is the framework of the carrier, i.e. the frame-like or cage-like framework or collection of the regenerated cartilage tissue by drilling may be considered.

The porous scaffold having the multilayer structure of this invention is a porous structural body constructed from two or more materials that are different from each other in any one of composition, porous structures such as a porosity, size of pores, and continuity of pores, mechanical property, and the like and are substantially not identical to each other but different from each other. These two materials may preferably be different in one or more of the composition, the porous structures, and the mechanical property and may include porous bodies having multilayer structures formed of porous structural bodies that are: different in composition and identical in other structures and properties; different in one or more of the porous structures such as porosity, size of pores, and continuity of pores; different only in dynamic properties; or different in two or more of the properties. The multilayer structure is formed by the two or more porous structural bodies that are linked to each other. The linkage of the multilayer structure may be formed by abutting, contacting, or laminating layers of the different porous structural bodies or by a particle location pattern, a location pattern in a two-dimensional area, an inclusion mode, or the like of the different porous structural bodies.

In this invention, each of the two or more porous structural bodies is appropriate for regeneration of each of the adjacent tissues.

A schema of the porous scaffold having the preferred multilayer structure is shown by way of example in FIG. 1.

That is, the porous scaffold is formed by a combination of two or three of a first porous body A, a second porous body B and a third porous body C that are linked to each other and layered. The porous membrane is located on the periphery. The first porous body A may be a composite porous body, i.e. a composite mesh body or a composite porous body, wherein a porous body containing at least one selected from the group consisting of the bioabsorbable natural polymer, the cell growth factor, the cell differentiation control factor, and the derivatives thereof is formed in the mesh body or the porous body formed of one or more of the bioabsorbable synthetic polymers as described above, i.e. in openings of the mesh body or in pores of the porous body, and the second porous body B and the third porous body C may be a combined porous body, i.e. a composite mesh body or a composite porous body, wherein a porous body containing at least one selected from the group consisting of the bioabsorbable natural polymer, the cell growth factor, the cell differentiation control factor, and the derivatives thereof is formed in the mesh body or the porous body formed of one or more of the bioabsorbable synthetic polymers as described above, i.e. in openings of the mesh body or in pores of the porous body. In the case where all of the first to third porous bodies are the composite mesh or the composite porous body, the porous bodies may preferably be different in at least one of composition of components, porous structures such as porosity, size of pores, and continuity of pores, and mechanical property. In the case where the first and second porous bodies or the third porous body are/is the composite mesh body or the composite porous body, the first and second porous bodies and the third porous body may preferably be different from each other in at least one of composition of components, porous structures such as porosity, size of pores, and continuity of pores, and mechanical property. In the case where the second and third porous bodies are the porous bodies containing at least one selected from the group consisting of the bioabsorbable natural polymer, the cell growth factor, the cell differentiation control factor, and the derivatives thereof, the second and third porous bodies may preferably be different from each other in at least one of composition of components, porous structures such as porosity, size of pores, and continuity of pores, and mechanical property.

The mesh body or the porous body to be used in this invention is used since it facilitates seeding of cells of identical or different types respectively in the layers of the porous body having the multilayer structure of this invention and regeneration of adjacent tissues such as cartilage and bone, epithelium and dermis, epithelium, dermis, and hypodermal tissue. The mesh body may be formed from a woven fabric, a knitted fabric, a woven cloth, an unwoven cloth, or the like. It is possible to obtain the porous body by known methods such as the foam molding method using a foaming agent, the freeze-drying method, and the porous agent removing method. In the foam molding method of the porous body, a foaming agent is added to a polymer compound to be foamed, and then the polymer is cured. An aqueous solution or a suspension of the polymer is frozen, followed by freeze-drying and a crosslinking treatment. Water-soluble sugar or salt is added to the polymer solution, and, after the curing, the water-soluble substance is washed with water to be eliminated.

Though mechanical strength is reduced with an increase in mesh size of the mesh or pore size of the porous body and porosity, since the seeded cells are retained by the pores of the porous body, the number of seeded cells in the porous body is increased with the increase in mesh size of the mesh or pore size of the porous body and porosity to thereby achieve more efficient regeneration of tissues such as a bone tissue, a cartilage tissue, and skin.

Accordingly, the mesh size of the mesh or the pore size of the porous body is appropriately decided depending on the cite of transplantation in a living body and in view of desired mechanical strength or elasticity or a regeneration rate of the bone tissue, the cartilage tissue, or the skin.

Figure 2:
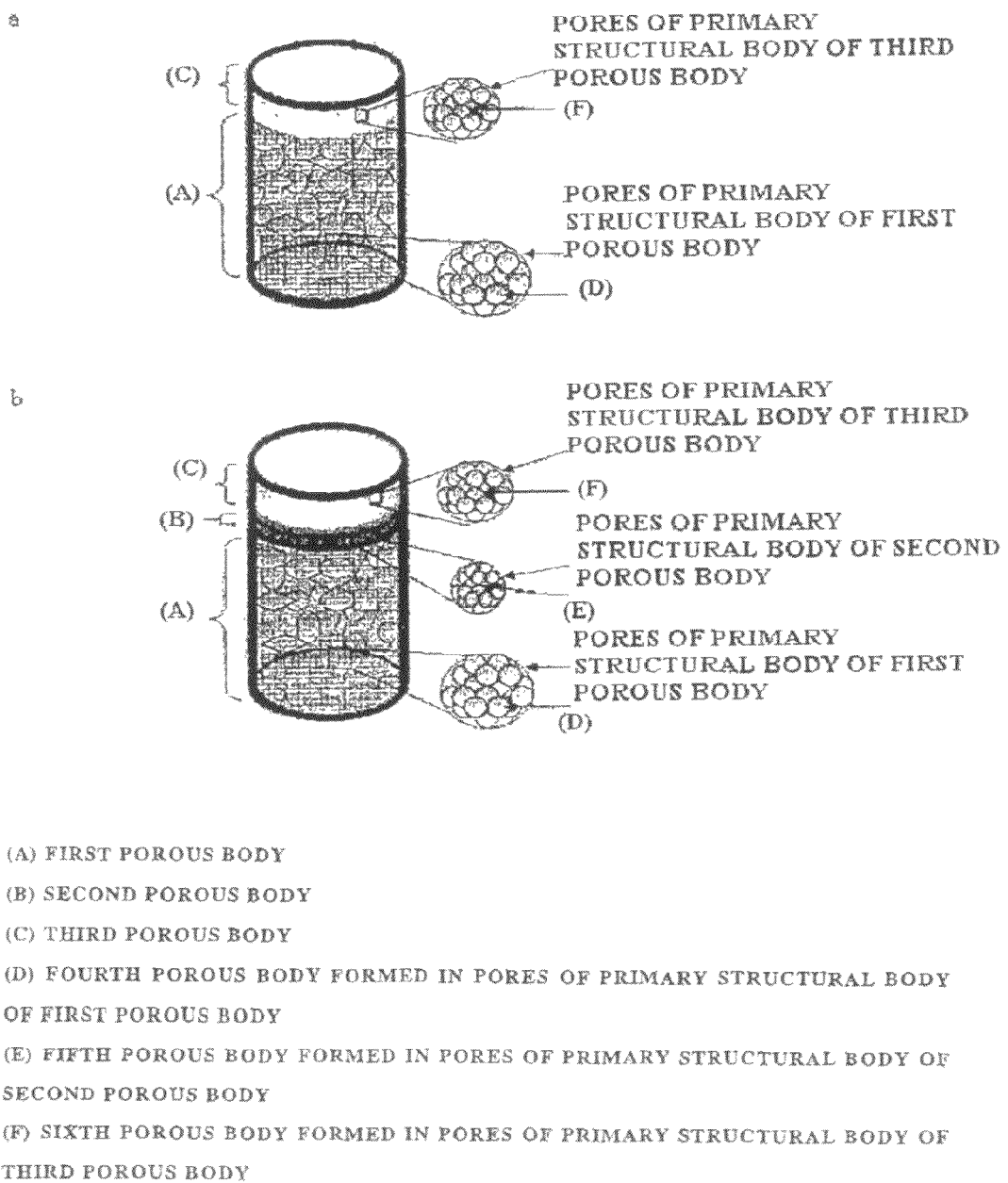
FIG. 2 is a diagram showing Representative Example 2 of the columnar porous scaffold covered with a porous membrane and having a multilayer structure.
Figure 3:
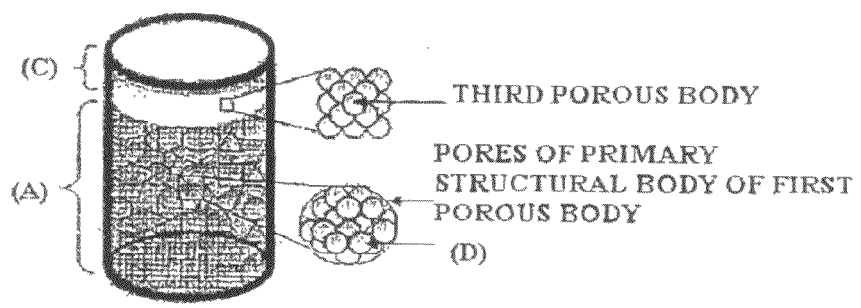
FIG. 3 is a diagram showing Representative Example 3 of the columnar porous scaffold covered with a porous membrane and having a multilayer structure.
Figure 3:
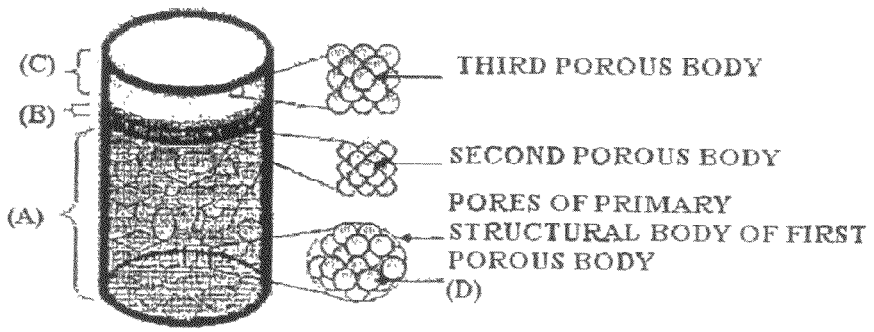

Preferred examples of the multiplayer structure of the porous scaffold of this invention are shown in FIGS. 2 and 3. Each of the first, second, and third porous bodies A, B, and C may preferably be a composite porous body, i.e. a composite mesh body or a composite porous body, wherein a porous body containing at least one selected from the group consisting of a bioabsorbable natural polymer, a cell growth factor, a cell differentiation control factor, and derivatives thereof is formed in a mesh body or porous body of one or more of the bioabsorbable synthetic polymers, i.e. in openings of the mesh body or pores of the porous body.

Preferred example of a method of producing the porous scaffold (FIG. 2a) of this invention is such that (1) a porous body of a bioabsorbable synthetic polymer which is the third porous body (C) is placed on a porous body of a bioabsorbable synthetic polymer which is the first porous body (A) to form a layered structure, (2) the first porous body (A) and the third porous body (C) are respectively impregnated with solutions each containing at least one of a bioabsorbable natural polymer, a cell growth factor, a cell differentiation control factor, and derivatives thereof to form a fourth porous body (D) and a sixth porous body (F) inside the first porous body (A) and the third porous body (C), respectively, and (3) the porous bodies are freeze-dried, preferably followed by a treatment with a gaseous or liquid crosslinking agent for crosslinking. Location of the porous membrane is as described above.

It is possible to perform Step (1) by using the bioabsorbable synthetic polymer and employing phase separation, particulate leaching, or foam molding. Two porous agents varied in diameter are mixed with a solution obtained by dissolving the bioabsorbable synthetic polymer into an organic solvent to prepare two types of porous agent/polymer solutions, and one of the porous agent/polymer solutions is placed on the other porous agent/polymer solution, followed by drying for eliminating the porous agents. Thus, the porous body of Step (1) is produced.

Examples of the bioabsorbable synthetic polymer include polylactic acid, polyglycolic acid, a copolymer of lactic acid and glycolic acid, poly-$\epsilon$-caprolactone, polyester or cellulose such as copolymers of the above bioabsorbable synthetic polymers, polysaccharide such as polyalginic acid, and the like that are described in the foregoing. Preferred among the above-described bioabsorbable synthetic polymers in this invention are the polylactic acid, the polyglycolic acid, the copolymer of lactic acid and glycolic acid, the poly-$\epsilon$-caprolactone, and the copolymers thereof.

Examples of the solvent for dissolving the bioabsorbable synthetic polymer include chloroform, carbon tetrachloride, dioxane, trichloroacetic acid, dimethylformamide, methylene chloride, ethyl acetate, acetone, hexafluoroisopropanol, dimethylacetoamide, hexafluoro-2-propanol, and the like.

Examples of the porous agent include a water-soluble carbohydrate such as a grape sugar and a sugar, particles and a crystal of a salt such as sodium chloride, potassium chloride, sodium tartrate, sodium citrate, ammonium carbonate, sodium carbonate, sodium bicarbonate, and the like.

Examples of a method for eliminating the porous agent include impregnation and washing with a pure water.

In Step (2), one or more of the bioabsorbable natural polymer, the cell growth factor, the cell differentiation control factor, and the derivatives thereof is mixed and impregnated or mixed.

In Step (2), the porous body produced by placing the porous body of the bioabsorbable synthetic polymer which is the third porous body (C) on the porous body of the bioabsorbable synthetic polymer which is the first porous body (A) is treated with the aqueous solution of the bioabsorbable natural polymer, the cell growth factor, the cell differentiation control factor, or the derivatives thereof. Various methods may be employed as a method of the treatment, and impregnation or coating may preferably be employed.

The impregnation is as described above. The coating is effective when the impregnation is not applicable due to a high concentration and viscosity of the aqueous solution of the bioabsorbable natural polymer, the cell growth factor, or the cell differentiation control factor and performed by applying the high concentration aqueous solution of the bioabsorbable natural polymer, the cell growth factor, or the cell differentiation control factor on the bioabsorbable synthetic polymer mesh body.

Preferred example of a method of producing the porous scaffold (FIG. 2b) of this invention is such that (1) a porous body of a bioabsorbable synthetic polymer which is the second porous body (B) is layered on a porous body of a bioabsorbable synthetic polymer which is the first porous body (A), and a porous body of a bioabsorbable synthetic polymer which is the third porous body (C) is layered on the second porous body (B), (2) the first porous body (A), the second porous body (B), and the third porous body (C) are respectively impregnated with solutions each containing at least one of a bioabsorbable natural polymer, a cell growth factor, a cell differentiation control factor, and derivatives thereof to form a fourth porous body (D), a fifth porous body (E), and a sixth porous body (F) inside the first porous body (A), the second porous body (B), and the third porous body (C), respectively, and (3) the porous bodies are freeze-dried, preferably followed by a treatment with a gaseous or liquid crosslinking agent for crosslinking. Location of the porous membrane is as described above.

It is possible to perform Step (1) by using the bioabsorbable synthetic polymer and employing phase separation, particulate leaching, or foam molding. Three porous agents varied in diameter are mixed with a solution obtained by dissolving the bioabsorbable synthetic polymer into an organic solvent to prepare three types of porous agent/polymer solutions. One of the porous agent/polymer solutions is applied on one of the remaining two porous agent/polymer solutions, and the remaining one porous agent/polymer solution is further applied, followed by drying and eliminating the porous agents. Thus, the porous body of Step (1) is produced.

Steps (2) and (3) are the same as those in the case of FIG. 2a.

Preferred example of a method of producing the porous scaffold (FIG. 3a) of this invention is such that (1) a porous body of a bioabsorbable synthetic polymer which is the first porous body (A) is produced, (2) the first porous body (A) is impregnated with a solution of one or more of a bioabsorbable natural polymer, a cell growth factor, a cell differentiation control factor, and derivatives thereof forming a secondary structural body in the first porous body, (3) an aqueous solution of one or more of a bioabsorbable natural polymer, a cell growth factor, a cell differentiation control factor, and derivatives thereof are applied, and (4) freeze-drying is performed, preferably followed by a treatment with a gaseous or liquid crosslinking agent for crosslinking. Location of the porous membrane is as described above.

It is possible to produce the porous body in Step (1) by using the bioabsorbable synthetic polymer and employing phase separation, particulate leaching, or foam molding. A porous agent is mixed with a solution obtained by dissolving the bioabsorbable synthetic polymer into an organic solvent, followed by drying and eliminating the porous agents. Thus, the porous body of Step (1) is produced.

In Step (2), at least one of the bioabsorbable natural polymer, the cell growth factor, the cell differentiation control factor, and the derivatives thereof is mixed and impregnated or mixed.

In Step (3), one or more of the bioabsorbable natural polymer, the cell growth factor, the cell differentiation control factor, and the derivatives thereof is mixed, and the mixture is softly added or applied on the first porous body (A) to which the high concentration solution of one or more of the bioabsorbable natural polymer, the cell growth factor, the cell differentiation control factor, and the derivatives thereof in Step (3) is applied. A weight concentration of the mixture of at least one of the bioabsorbable natural polymer, the cell growth factor, the cell differentiation control factor, and the derivatives thereof is 0.05% to 3%. The most desirable concentration is 0.1% to 2%.

Preferred example of a method of producing the structural body (FIG. 3b) of this invention is such that (1) a porous body of a bioabsorbable synthetic polymer which is the first porous body (A) is produced, (2) the first porous body (A) is impregnated with a solution of one or more of a bioabsorbable natural polymer, a cell growth factor, a cell differentiation control factor, and derivatives thereof forming a secondary structural body in the first porous body (A), (3) an aqueous solution of one or more of a bioabsorbable natural polymer, a cell growth factor, a cell differentiation control factor, and derivatives thereof are applied on the first porous body (A), (4) an aqueous solution of one or more of a bioabsorbable natural polymer, a cell growth factor, a cell differentiation control factor, and derivatives thereof are further applied, and (5) freeze-drying is performed, preferably followed by a treatment with a gaseous or liquid crosslinking agent for crosslinking. Location of the porous membrane is as described above.

It is possible to produce the porous body in Step (1) by using the bioabsorbable synthetic polymer and employing phase separation, particulate leaching, or foam molding. A porous agent is mixed with a solution obtained by dissolving the bioabsorbable synthetic polymer into an organic solvent, followed by drying and eliminating the porous agents. Thus, the porous body of Step (1) is produced.

In Step (2), one or more of the bioabsorbable natural polymer, the cell growth factor, the cell differentiation control factor, and the derivatives thereof is mixed and impregnated or mixed.

In Step (3), one or more of the bioabsorbable natural polymer, the cell growth factor, the cell differentiation control factor, and the derivatives thereof having the higher concentration is mixed, and the mixture is softly added or applied on the first porous body (A) which is impregnated with the solution of one or more of the bioabsorbable natural polymer, the cell growth factor, the cell differentiation control factor, and the derivatives thereof in Step (2) to deposit the solution in the first porous body (A). A weight concentration of the mixture of at least one of the bioabsorbable natural polymer, the cell growth factor, the cell differentiation control factor, and the derivatives thereof is 0.1% to 5%. The most desirable concentration is 0.3% to 5%.

In Step (4), one or more of the bioabsorbable natural polymer, the cell growth factor, the cell differentiation control factor, and the derivatives thereof is mixed, and the mixture is softly added or applied on the first porous body (A) to which the high concentration solution of one or more of the bioabsorbable natural polymer, the cell growth factor, the cell differentiation control factor, and the derivatives thereof in Step (3) is applied. A weight concentration of the mixture of at least one of the bioabsorbable natural polymer, the cell growth factor, the cell differentiation control factor, and the derivatives thereof is 0.05% to 3%. The most desirable concentration is 0.1% to 2%.

EXAMPLES

Hereinafter, this invention will be described in more details by using examples. This invention is not of course limited by the following examples.

Example 1

As one example, a porous body having a frame formed from a polyethylene cylinder frame and a nylon mesh and a PLGA-collagen composite sponge/collagen sponge formed of a composite sponge (PLGA-collagen composite sponge) part of a copolymer (PLGA) of lactic acid and glycolic acid and a porcine skin-derived pepsin solubilized type I collagen which is a bioabsorbable natural polymer and a porcine skin-derived pepsin solubilized type I collagen sponge part was prepared, wherein the PLGA-collagen composite sponge/collagen sponge had a layered structure and was introduced into the frame.

The nylon mesh having pores each having a diameter of 2 μm was adhered by heat to a bottom face and an inner surface of the polyethylene cylinder frame having an inner diameter of 6 mm to produce a frame-like structure as a framework of a porous scaffold. The thus-produced framework was washed with an alkaline water and rinsed with a ultrapure water, followed by drying.

Particles of sodium chloride having a diameter of 355 to 425 μm were obtained by sifting with sieves having mesh openings of 355 μm and 425 μm. The copolymer PLGA of lactic acid and glycolic acid (75:25) was dissolved into chloroform to prepare a 15(w/v) %-solution.

The PLGA chloroform solution was poured into an aluminum pan, and the particles of sodium chloride having the diameter of 355 to 425 μm were added to the solution, followed by mixing well and drying in the air for 48 hours. After the drying, a column of sodium chloride/PLGA having a diameter of 6.0 mm was obtained by drilling by using a cork poler having an inner diameter of 6.0 mm. The sodium chloride/PLGA column was placed in a distilled water, and the distilled water was replaced every two hours. This washing was continued for 4 days. Thus, a PLGA sponge column having a pore diameter of 355 to 425 μm and a porosity of 90% was obtained.

After drying the PLGA sponge column for 24 hours in the air, drying in a vacuum state was continued for 12 hours. After that, the PLGA sponge column was impregnated with a 1.0 wt %-pig skin-derived pepsin solubilized type I collagen acidic aqueous solution (pH=3.0), and the pig skin-derived pepsin solubilized type I collagen aqueous solution was allowed to occupy the pores of the PLGA sponge in a vacuum state. The PLGA sponge column filled with the pig skin-derived pepsin solubilized type I collagen aqueous solution was placed into the framework of the polyethylene cylinder frame and the nylon mesh, and a 1.0 wt %-pig type I atelocollagen acidic aqueous solution was poured into an upper end, followed by freezing at −80° C. for 12 hours.

After the freezing, freeze-drying was performed in a vacuum state at a reduced pressure (0.2 Torr) for 24 hours to form a collagen sponge in the PLGA sponge in the framework of the polyethylene cylinder frame and the nylon mesh as well as to form a collagen sponge at one end of the PLGA sponge.

Figure 6:
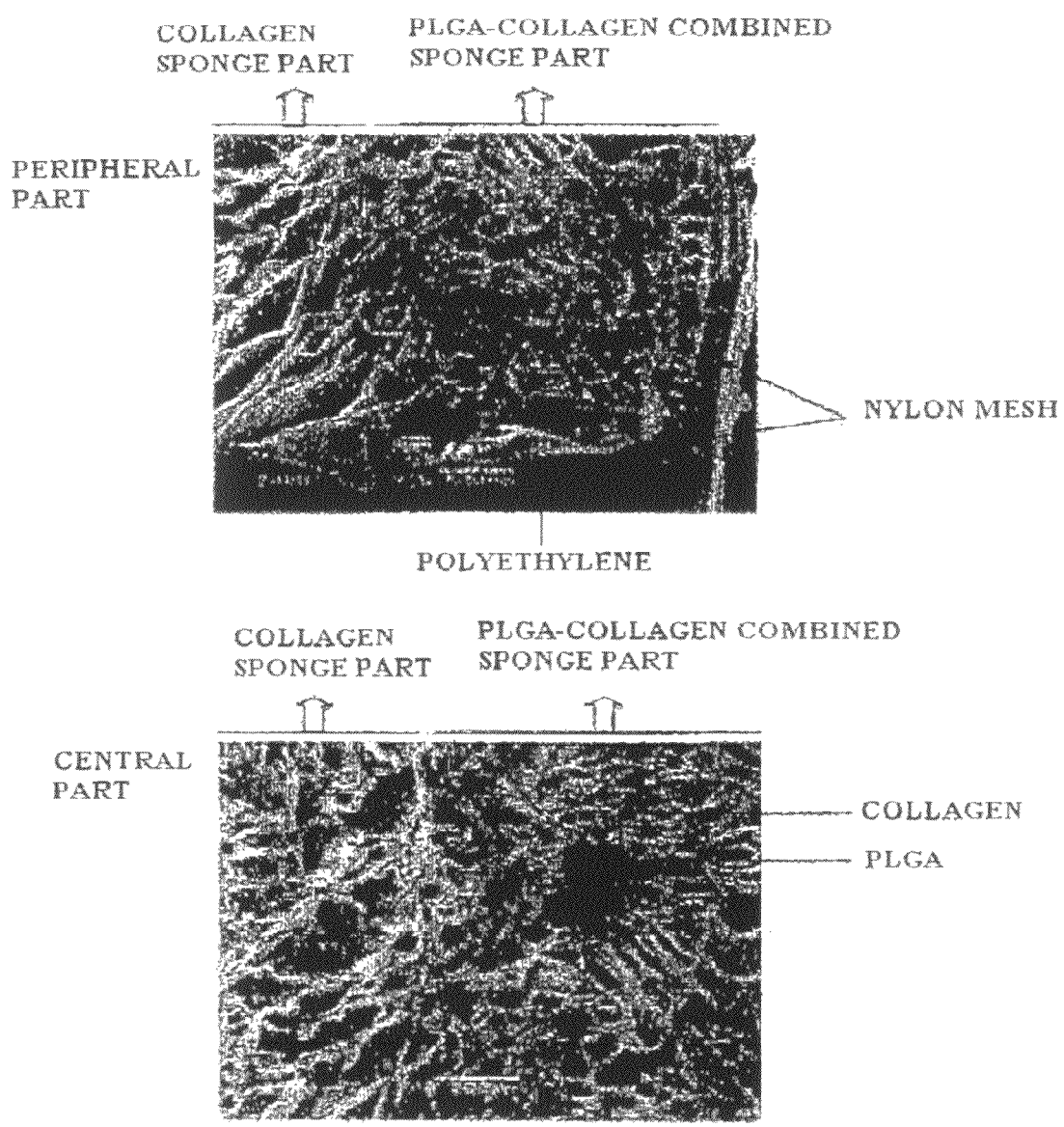
FIG. 6 is a diagram showing electronmicroscopic photographs of a peripheral part (above) and a central part (below) of a composite porous body having a multilayer structure of a collagen sponge and PLGA-collagen composite sponge, which is formed in a cylinder frame of polyethylene and a nylon mesh.

The thus-produced material was subjected to a crosslinking treatment with a gultaraldehyde vapor saturated with a 25 wt %-gultaraldehyde aqueous solution at 37° C., followed by washing with a distilled water for 5 times. The material was treated with a 0.1 M-glycine aqueous solution for 24 hours, followed by washing with a distilled water for 20 times. The material was frozen at −80° C. for 12 hours and freeze-dried in a vacuum state under a reduced pressure (0.2 Torr) for 24 hours to prepare the PLGA-collagen composite sponge/collagen sponge having the layered structure wherein the cologne sponge is formed in the PLGA sponge in the framework of the polyethylene cylinder frame and the nylon mesh and the collagen sponge is formed at one end of the PLGA sponge. The thus-obtained PLGA-collagen composite sponge/collagen sponge having the layered structure was coated with gold, and the structure was observed by scanning electronmicroscopy (SEM). SEM photographs are shown in FIG. 6.

Example 2

As one example, a porous body having a frame formed from a polyethylene cylinder frame and a nylon mesh and a sponge of a porcine type I atelocollagen which is a bioabsorbable natural polymer was prepared, wherein the sponge was introduced into the frame.

The nylon mesh having pores each having a diameter of 2 μm was adhered by heat to a bottom face and an inner surface of the polyethylene cylinder frame having an inner diameter of 6 mm to produce the frame as a framework of a porous scaffold. The thus-produced framework was washed with an alkaline water and rinsed with a ultrapure water, followed by drying.

The thus-produced framework was impregnated with a porcine skin-derived pepsin solubilized type I collagen acid aqueous solution and left in a vacuum state under a reduced pressure that does not freeze the aqueous solution to defoam the framework and to fill the framework with the collagen aqueous solution. The framework filled with the collagen aqueous water was frozen at −80° C. for 6 hours. The frozen material was freeze-dried in a vacuum state under a reduced pressure (0.2 Torr) for 48 hours to produce a non-crosslinked scaffold material wherein a collagen sponge is formed in the framework.

The thus-obtained non-crosslinked scaffold material was subjected to a crosslinking treatment with a gultaraldehyde vapor saturated with a 25 wt %-gultaraldehyde aqueous solution at 37° C. and washed with a phosphoric acid buffer solution for 10 times. The material was impregnated with a 0.1 M-glycine aqueous solution for 4 hours, followed by washing with a phosphoric acid buffer solution for 10 times. After washing with a distilled water for 3 times, the material was frozen at −80° C. for 12 hours. The material was freeze-dried in a vacuum state under a reduced pressure (0.2 Torr) for 24 hours to obtain a porous scaffold for cells of this invention as a scaffold material.

Figure 7:
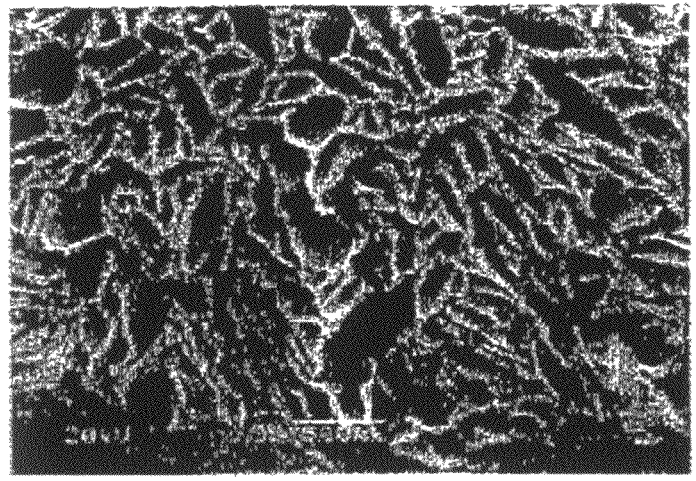
FIG. 7 is a diagram showing electronmicroscopic photographs of a peripheral part (above) and a central part (below) of a composite porous body formed of a collagen sponge that was formed in a cylinder frame of polyethylene and a nylon mesh.
Figure 7:
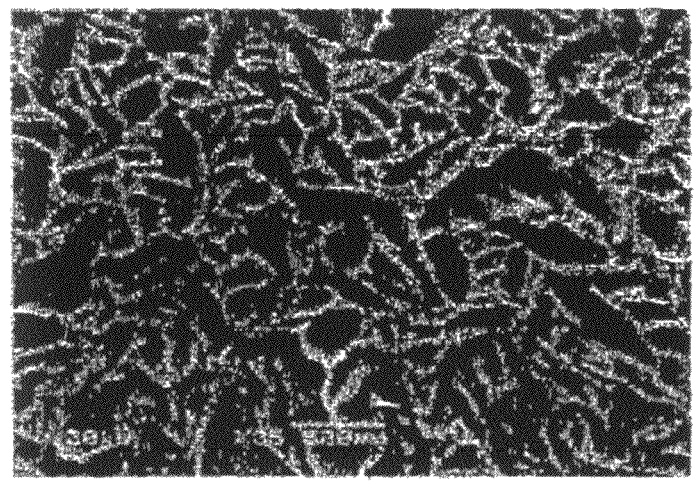

The thus-obtained porous scaffold was coated with gold, and the structure was observed with scanning electronmicroscopy (SEM). SEM photographs are shown in FIG. 7.

Example 3

With the use of the porous body prepared by Example 2, regeneration of a cartilage tissue by culturing human bone marrow-derived mesenchymal stem cells was performed.

Passage culture of human born marrow-derived mesenchymal stem cells purchased from Cambrex (Cambrex BioScience Walkersville, Inc.) was performed twice at a temperature of 37° C. and under a 5%-$CO_2$ atmosphere in a proliferation medium purchased from Cambrex (Cambrex BioScience Walkersville, Inc.) (a basic medium for mesenchymal stem cells to which a 10%-fetal bovine serum, penicillin/streptomycin, and L-glutamine were added). The bone marrow cells after the passage cultures were detached and collected by using 0.025%-trypsin/0.01%-EDTA/PBS(−) to prepare $1.5 \times 10^6$ cells/mL of a bone marrow cell suspension solution. Next, 1,000 μl of the cell suspension solution was added by dropping to the three-dimensional porous material that was sterilized with an ethylene oxide gas to seed the cells. After the seeding, the solution leaked out the porous scaffold was collected, and the number of cells was counted. As a result, a seeding efficiency of the seeded cells was 95.2±1.0%, which is considerably high. After that, the porous scaffold to which the cells were seeded were transferred to a T75 culture flask, and 50 mL of an MSC proliferation medium was added to the flask to conduct a culture with shaking for a week. After the 1-week culture, the medium was replaced with a DMEM differentiation medium that did not contain any serum and contained an antibiotics, 4,500 mg/L of glucose, 584 mg/L of glutamine, 0.4 mM of proline, 50 mg/L of ascorbic acid, 100 nM of dexamethasone, and 10 ng/mL of TGF β3 to further conduct a culture for 4 weeks to regenerate a cartilage tissue.

Figure 8:
FIG. 8 is a diagram showing histological stained photographs of a cartilage tissue obtained by culturing bone marrow-derived mesenchymal stem cells in the porous scaffold. A: hematoxylin and eosin staining, B: Safranin-O staining, C: toluidine blue staining.
Figure 8:
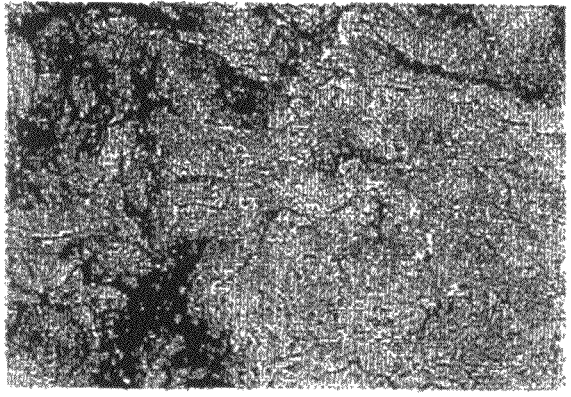
Figure 8:
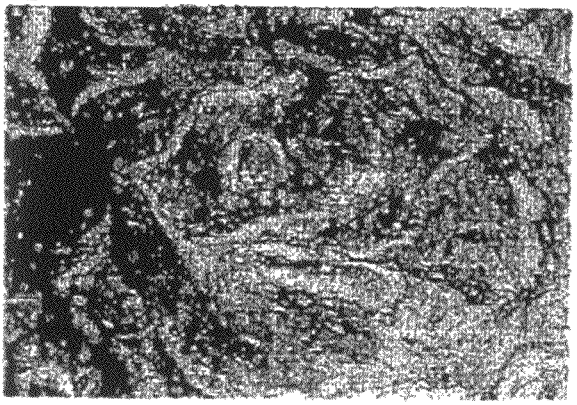

Shown in FIG. 8 are photographs of results of HE (hematoxylin and eosin) staining, Safranin-O staining, and toluidine blue staining of the thus-regenerated tissue, from which it is possible to confirm round cells and safranin-O-stainable and toluidine blue-stainable extracellular matrix.

The invention claimed is:

1. A porous scaffold for seeding cells, the porous scaffold comprising:
   a framework which is a cylinder frame formed of polyethylene and a nylon mesh;
   a main body located within the framework, the main body being a porous body having a pore size when enables cell seeding; and
   a porous membrane including pores having a pore size smaller than the size of the cells,
   wherein an outer peripheral surface of the porous scaffold is covered with the porous membrane,
   wherein the main body has an entrance for seeding cells which is not covered with the porous membrane,
   wherein the main body has a multilayer structure comprising layers, and each layer is a porous body comprising at least one selected from the group consisting of a bioabsorbable synthetic polymer, a bioabsorbable natural polymer, a cell growth factor, a cell differentiation control factor, and derivatives thereof,
   wherein the layers are stacked in an axial direction of the cylinder frame,
   wherein the layers forming the multilayer structure are different in at least one characteristic selected from the group consisting of composition, porous structure including porosity, size of pores, continuity of pores, and mechanical property,
   wherein the pore size of the porous body is from 20 to 400 μm, and
   wherein the pore size of the porous membrane is from 0.45 to 10 μm.

2. A method of forming tissue comprising:
   providing the porous scaffold of claim 1;
   seeding cells through the entrance; and
   supporting chondrocytes or stem cells differentiating into chondrocytes in the main body.

3. A method of forming tissue comprising:
providing the porous scaffold of claim 1;
seeding cells through the entrance; and
supporting cells in the main body.

* * * * *